US012797316B2

(12) United States Patent
Yuki et al.

(10) Patent No.: US 12,797,316 B2
(45) Date of Patent: Nov. 17, 2026

(54) AEROSOL TYPE COSMETIC HAIR PREPARATION

(71) Applicant: KAO CORPORATION, Tokyo (JP)

(72) Inventors: Katsuyuki Yuki, Sumida-ku (JP); Akiko Mieno, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 562 days.

(21) Appl. No.: 18/000,076

(22) PCT Filed: Apr. 5, 2021

(86) PCT No.: PCT/JP2021/014430
§ 371 (c)(1),
(2) Date: Nov. 28, 2022

(87) PCT Pub. No.: WO2021/241005
PCT Pub. Date: Dec. 2, 2021

(65) Prior Publication Data

US 2023/0210734 A1 Jul. 6, 2023

(30) Foreign Application Priority Data

May 29, 2020 (JP) ................................. 2020-094431

(51) Int. Cl.

| | |
|---|---|
| ***A61K 8/36*** | (2006.01) |
| ***A61K 8/04*** | (2006.01) |
| ***A61K 8/46*** | (2006.01) |
| ***A61Q 5/02*** | (2006.01) |

(52) U.S. Cl.
CPC ................ *A61K 8/36* (2013.01); *A61K 8/046* (2013.01); *A61K 8/466* (2013.01); *A61Q 5/02* (2013.01)

(58) Field of Classification Search
None
See application file for complete search history.

(56) References Cited

U.S. PATENT DOCUMENTS

| | | | | |
|---|---|---|---|---|
| 7,776,806 | B2 | 8/2010 | Tokunaga | |
| 2009/0178210 | A1* | 7/2009 | Bistram | A61K 8/39 8/431 |
| 2014/0044760 | A1* | 2/2014 | Lei | A61Q 15/00 510/276 |
| 2015/0272834 | A1* | 10/2015 | Sun | A61P 17/00 424/490 |
| 2017/0216165 | A1* | 8/2017 | Traynor | A01N 25/28 |

FOREIGN PATENT DOCUMENTS

| | | | |
|---|---|---|---|
| EP | 3 831 359 | A1 | 6/2021 |
| JP | 61-43102 | A | 3/1986 |
| JP | 8-73839 | A | 3/1996 |
| JP | 2001-507034 | A | 5/2001 |
| JP | 2001-288049 | A | 10/2001 |
| JP | 2002-128644 | A | 5/2002 |
| JP | 2005-239570 | A | 9/2005 |
| JP | 2013-213062 | A | 10/2013 |
| JP | 2014-129307 | A | 7/2014 |
| KR | 10-2014-0058329 | A | 5/2014 |
| WO | WO 2020/027177 | A1 | 2/2020 |

OTHER PUBLICATIONS

JP 2005-239570 English Translation (Year 2005).*
JP 61-43102 English Translation (Year 1986).*
Extended European Search Report issued Jun. 21, 2024 in European Patent Application No. 21813949.1, 6 pages.
International Search Report issued Jun. 22, 2021 in PCT/JP2021/014430, filed on Apr. 5, 2021, 3 pages.

* cited by examiner

*Primary Examiner* — David J Blanchard
*Assistant Examiner* — Sarah J Chickos
(74) *Attorney, Agent, or Firm* — Oblon, McClelland, Maier & Neustadt, L.L.P.

(57) ABSTRACT

An aerosol cosmetic hair preparation including a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less. The component (B) comprises an aromatic sulfonic acid or a salt thereof.

15 Claims, 1 Drawing Sheet

AEROSOL TYPE COSMETIC HAIR PREPARATION

CROSS REFERENCE TO RELATED APPLICATIONS

This application is a National Stage entry under 35 U.S.C. § 371 of PCT/JP2021/014430, filed on Apr. 5, 2021, and claims priority to Japanese Patent Application No. 2020-094431, filed on May 29, 2020. The entire contents of both are incorporated herein by reference.

FIELD OF THE INVENTION

The present invention relates to an aerosol type cosmetic hair preparation.

BACKGROUND OF THE INVENTION

Aerosol type cosmetic preparations have an advantage that the cosmetic preparation as an aerosol stock solution can be easily coated and spread on the skin or the hair to allow the active ingredient in the cosmetic preparation to penetrate effectively into the skin or the hair since the cosmetic preparation can be used by discharging in the form of foam.

In the field of aerosol type cosmetic preparations, the improvement of adherability of the skin or hair care ingredient has been investigated. For example, Patent Literature 1 (JP 2001-507034 T) describes that a cleansing product for human use including a foamable composition having a prescribed viscosity containing a prescribed amount of water and a prescribed amount of a specific surfactant, a propellant gas containing carbon dioxide, nitrous oxide, or a mixture thereof, and a container can improve the foamability, mildness, the adherability and the like of the skin/hair care ingredient on the skin. There is also described that the foamable composition contains approximately 1 to approximately 50% by weight of a water insoluble skin or hair care ingredient.

SUMMARY OF THE INVENTION

The present invention relates to an aerosol type cosmetic hair preparation containing a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less.

DETAILED DESCRIPTION OF THE INVENTION

[Aerosol Type Cosmetic Hair Preparation]

Figure 1:
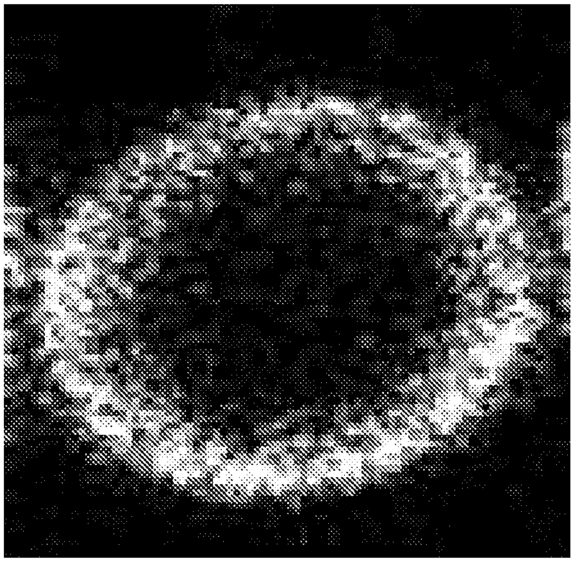
FIG. 1 is a mapping image obtained through analysis by TOF-SIMS of p-toluenesulfonic acid existing on the cross section of the hair cleansed with the hair cleansing agent of Example 6.

The aerosol type cosmetic hair preparation of the present invention (which may be hereinafter referred simply to as a "cosmetic hair preparation of the present invention") contains a cosmetic hair preparation stock solution containing a surfactant (A) and an organic acid except for citric acid, or a salt thereof (B), and a propellant (C) containing carbon dioxide, and has a pH at 20° C. of 3.0 or more and 5.0 or less. The use of the cosmetic hair preparation of the present invention can allow the organic acid as an active ingredient for the hair reformation to penetrate into the inside of the hair efficiently.

In the present invention, the expression "to have a component X" and "to contain a component X" also mean "to be formed by mixing a component X".

The known aging-related changes of the hair include the decrease of the hair diameter, the increase of white hair, the decrease of bounce and resilience, and the increase of the hair with wavy form (curly hair). It has known that the decrease of the bounce and resilience leads the decrease of the hair volume, and the curly hair leads the deterioration of manageability of the hair and the decrease of the hair gloss, resulting in problems of the hair.

Various investigations have been made for physical measures and chemical measures relating to techniques for solving the problems of the hair, and the penetration of the active ingredient into the inside of the hair for reforming the hair from the inside thereof has been recognized as an important technique. Examples of the active ingredient having been used include an organic acid, such as malic acid (for imparting bounce and resilience) and p-toluenesulfonic acid (for improving the wavy form).

However, the skin or hair care ingredient described in Patent Literature 1 is a water insoluble component, such as a cosmetic oil, and there is no description therein about the penetration technique for an organic acid, which is an active ingredient for the hair reformation and is a water soluble component.

An object of the present invention is to provide an aerosol type cosmetic hair preparation that can allow an organic acid, which is an active ingredient for the hair reformation, to penetrate efficiently into the inside of the hair.

The present inventors have found that the problem can be solved by an aerosol type cosmetic hair preparation that contains a cosmetic hair preparation stock solution containing a surfactant and an organic acid except for citric acid, or a salt thereof, and a propellant containing carbon dioxide, and has a pH within the prescribed range.

According to the present invention, an aerosol type cosmetic hair preparation that can allow an organic acid, which is an active ingredient for the hair reformation, to penetrate efficiently into the inside of the hair ban be provided.

The mechanism that the cosmetic hair preparation of the present invention can exhibit the effects of the present invention having the aforementioned configuration thereof is still not clear, but can be estimated as follows.

The cosmetic hair preparation stock solution, which is an aerosol stock solution, used in the aerosol type cosmetic hair preparation of the present invention contains a surfactant (A) and an organic acid except for citric acid, or a salt thereof (B).

The surfactant as the component (A) is used for imparting the dischargeability of foam through aerosol effect and the target capability as the cosmetic hair preparation.

The organic acid or a salt thereof as the component (B) is used as an active ingredient for reforming the hair. It is considered that the penetration of an organic acid into the inside of the hair can enhance the bounce and resilience of the inside of the hair through increase of the flexural elasticity of the inside of the hair, and can suppress the wavy form of the hair through stress relaxation inside the hair.

The aerosol type cosmetic hair preparation of the present invention also contains a propellant (C) containing carbon dioxide. Carbon dioxide as a propellant enables the discharge of fine dense foam, and the active ingredient in the discharged cosmetic hair preparation can be uniformly coated on the hair. Furthermore, it is considered that carbon dioxide gas dissolved in the foam acts on the hair to facilitate the penetration of the organic acid into the inside of the hair.

The dissociation state of carbon dioxide is changed in accordance with the pH of the liquid having carbon dioxide dissolved therein, and with a higher pH value, carbon dioxide releases hydrogen ion to exist as hydrogencarbonate ion. In the case where the pH of the cosmetic hair preparation at 20° C. is 3.0 or more and 5.0 or less, it is considered that the proportion of carbon dioxide molecules in the cosmetic hair preparation is increased to enhance the effect of facilitating the penetration of the organic acid by carbon dioxide gas.

The cosmetic hair preparation of the present invention has a pH at 20° C. of 3.0 or more and 5.0 or less. The pH is a pH of an aqueous solution at 20° C. obtained in such a manner that the aerosol type cosmetic hair preparation containing the cosmetic hair preparation stock solution and the propellant (C) is discharged from an aerosol container and then diluted 20 times with water.

The pH at 20° C. of the cosmetic hair preparation is preferably 3.2 or more, and more preferably 3.4 or more, and is preferably 4.8 or less, more preferably 4.5 or less, and further preferably 4.2 or less, from the standpoint of the enhancement of the effect of facilitating the penetration of the organic acid into the inside of the hair. Specific range of the pH at 20° C. of the cosmetic hair preparation is 3.0 to 5.0, preferably 3.0 to 4.8, more preferably 3.0 to 4.5, further preferably 3.0 to 4.2, still further preferably 3.2 to 4.2, and still more further preferably 3.4 to 4.2.

The pH of the cosmetic hair preparation can be specifically measured by the method described in the examples.

In the present invention, the increment rate of the flexural elastic modulus or the stress relaxation rate of the hair after the treatment with the cosmetic hair preparation is used as an index of the effect of facilitating the penetration of the organic acid into the inside of the hair. A higher increment rate of the flexural elastic modulus of the hair after the treatment, or a higher increment rate of the stress relaxation rate of the hair after the treatment means a higher effect of facilitating the penetration of the organic acid. The increment rates of the flexural elastic modulus and the stress relaxation of the hair after the treatment can be specifically measured by the method described in the examples.

Examples of the cosmetic hair preparation of the present invention include a hair cleansing agent, such as a shampoo, a hair conditioning agent, a hair treatment agent (including a non-rinse type), a hair styling agent, a hair dye, and a hair growth agent. Among these, a hair cleansing agent is preferred in the case where the component (A) described later mainly contains an anionic surfactant or a nonionic surfactant. A hair conditioning agent, a hair treatment agent, and a hair styling agent are preferred in the case where the component (A) described later mainly contains a cationic surfactant.

The aerosol type cosmetic hair preparation of the present invention is preferably an aerosol type hair cleansing agent from the standpoint of the more effective exhibition of the effects of the present invention.

<Component (A): Surfactant>

The cosmetic hair preparation stock solution constituting the cosmetic hair preparation of the present invention contains a surfactant as a component (A). The component (A) is used for imparting the dischargeability of foam through aerosol effect and the target capability of the cosmetic hair preparation, and may be appropriately selected from an anionic surfactant, a cationic surfactant, a nonionic surfactant, and an amphoteric surfactant, corresponding to the kind of the cosmetic hair preparation.

In the case where the cosmetic hair preparation of the present invention is a hair cleansing agent, the component (A) preferably contains one or more kind selected from the group consisting of an anionic surfactant and a nonionic surfactant from the standpoint of imparting the cleansing capability.

(Anionic Surfactant)

Examples of the anionic surfactant include an alkylbenzene sulfonate salt, an alkyl or alkenyl ether sulfate salt, an alkyl or alkenyl sulfate salt, an alkyl sulfonate salt, a saturated or unsaturated fatty acid salt, an alkyl or alkenyl ether carboxylate salt, an α-sulfo fatty acid salt, an N-acylamino acid salt, a phosphoric acid mono- or diester salt, and a sulfosuccinic acid ester salt, and one kind or two or more kinds thereof may be used.

The hydrocarbon group, such as the alkyl group and the alkenyl group, and the constitutional fatty acid of the anionic surfactant preferably has 8 or more and 22 or less carbon atoms, more preferably 8 or more and 18 or less carbon atoms, and further preferably 10 or more and 18 or less carbon atoms.

Examples of the counter ion of the anionic group of the anionic surfactant include an alkali metal ion, such as sodium ion and a potassium ion; an alkaline earth metal ion, such as a calcium ion and magnesium ion; an ammonium ion; and an alkanolammonium having 1 to 3 alkanol group having 2 or 3 carbon atoms (such as monoethanolammonium, diethanolammonium, triethanolammonium, and triisopropanolammonium).

Among the above, the anionic surfactant is preferably one or more kind selected from the group consisting of an alkyl sulfate salt, an alkyl ether sulfate salt, an alkyl ether carboxylate salt, and an N-acylamino acid salt from the standpoint of the use as a hair cleansing agent. Examples of the alkyl sulfate salt include sodium lauryl sulfate. Examples of the alkyl ether sulfate salt include a polyoxyethylene alkyl ether sulfate salt, such as sodium laureth sulfate and ammonium laureth sulfate, and examples of the alkyl ether carboxylate salt include a polyoxyethylene alkyl ether acetate, such as sodium laureth acetate. Examples of the N-acylamino acid salt include an N-acylglutamate, such as sodium cocoyl glutamate.

The anionic surfactant is more preferably one or more kind selected from the group consisting of an alkyl ether sulfate salt and an N-acylamino acid salt, and further preferably one or more kind selected from the group consisting of sodium laureth sulfate, ammonium laureth sulfate, and sodium cocoyl glutamate.

(Nonionic Surfactant)

Examples of the nonionic surfactant include a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, a higher fatty acid sucrose ester, a polyglycerin fatty acid ester, a polyoxyalkylene hydrogenated castor oil, and an alkylsaccharide, and one kind or two or more kinds thereof may be used.

In the nonionic surfactants exemplified above, the average addition molar number of ethylene oxide (which may be hereinafter referred to as an "EO average addition molar number") of the polyoxyethylene alkyl ether, the polyoxyethylene alkenyl ether, the polyoxyethylene sorbitan fatty acid ester, the polyoxyethylene fatty acid ester, and the polyoxyethylene hydrogenated castor oil is preferably 2 or more, more preferably 3 or more, further preferably 5 or more, still further preferably 6 or more, and still more further preferably 8 or more, and is preferably 150 or less, and more preferably 80 or less. The EO average addition molar number is preferably 2 or more and 150 or less, and more preferably 3 or more and 80 or less. The EO average addition number is a number average value.

The alkyl group in the polyoxyalkylene alkyl ether, the alkyl glucoside, the alkyl alkanolamide, the alkyl glyceryl ether, and the alkylsaccharide, the alkenyl group in the polyoxyalkylene alkenyl ether, and the fatty acid in the polyoxyalkylene sorbitan fatty acid ester, polyoxyalkylene fatty acid ester, the higher fatty acid sucrose esters, and the polyglycerin fatty acid ester each preferably have 8 or more and 22 or less carbon atoms, and more preferably 8 or more and 18 or less carbon atoms.

Among the above, the nonionic surfactant is preferably one or more kind selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, and a polyoxyalkylene hydrogenated castor oil, more preferably one or more kind selected from the group consisting of a polyoxyalkylene alkyl ether, an alkyl glucoside, an alkyl alkanolamide, an alkyl glyceryl ether, and a polyoxyalkylene hydrogenated castor oil, and further preferably a polyoxyalkylene hydrogenated castor oil, from the standpoint of the use as a hair cleansing agent.

(Cationic Surfactant)

Examples of the cationic surfactant include (i) an alkyltrimethylammonium salt, (ii) an alkoxyalkyltrimethylammonium salt, (iii) a dialkyldimethylammonium salt, (iv) an alkylamidoalkyltrimethylammonium salt, (v) an alkyldimethylamine and a salt thereof, (vi) an alkoxyalkyldimethylamine and a salt thereof, and (vii) an alkylamidoalkyldimethylamine and a salt thereof, and one kind or two or more kinds thereof may be used.

The cationic surfactant preferably has a long-chain alkyl group having 8 or more and 22 or less carbon atoms, more preferably 8 or more and 18 or less carbon atoms, and further preferably 12 or more and 18 or less carbon atoms.

Examples of the salts of the amines (v) to (vii) include salts with an organic acid or an inorganic acid. Examples of the organic acid include an aliphatic monocarboxylic acid, such as acetic acid and a propionic acid; an aliphatic dicarboxylic acid, such as malonic acid, succinic acid, glutaric acid, adipic acid, maleic acid, and fumaric acid; an aromatic dicarboxylic acid, such as phthalic acid and isophthalic acid; a polycarboxylic acid, such as polyglutamic acid; a hydroxycarboxylic acid, such as glycolic acid, lactic acid, hydroxyacrylic acid, glyceric acid, malic acid, tartaric acid, and citric acid; and an acidic amino acid, such as glutamic acid and aspartic acid. Examples of the inorganic acid include hydrochloric acid, sulfuric acid, and phosphoric acid.

(Amphoteric Surfactant)

Examples of the amphoteric surfactant include a betaine type surfactant, an amine oxide type surfactant, and an amino acid type surfactant, and one kind or two or more kinds thereof may be used.

Examples of the betaine type surfactant include a carboxy betaine type, such as an alkyldimethylaminoacetic acid betaine and a fatty acid amidopropyl betaine; a sulfo betaine type, such as an alkylsulfo betaine and an alkylhydroxysulfo betaine; an imidazoline based betaine type; and a phospho betaine type.

The hydrocarbon group, such as the alkyl group and the alkenyl group, and the constitutional fatty acid of the amphoteric surfactant each preferably have 8 or more and 22 or less carbon atoms, more preferably 8 or more and 18 or less carbon atoms, and further preferably 12 or more and 18 or less carbon atoms.

The content of the component (A) in the cosmetic hair preparation stock solution is preferably 0.05% by mass or more, more preferably 0.10% by mass or more, and further preferably 0.20% by mass or more, from the standpoint of the dischargeability of foam through aerosol effect and the target capability as the cosmetic hair preparation, and is preferably 30% by mass or less, more preferably 20% by mass or less, and further preferably 15% by mass or less, from the standpoint of the enhancement of the storage stability. The specific range of the component (A) in the cosmetic hair preparation stock solution is preferably 0.05 to 30% by mass, more preferably 0.10 to 20% by mass, and further preferably 0.20 to 15% by mass.

In the case where the component (A) contains an anionic surfactant, the content of the anionic surfactant in the cosmetic hair preparation stock solution is preferably 0.50% by mass or more, more preferably 1.0% by mass or more, further preferably 3.0% by mass or more, still further preferably 5.0% by mass or more, and still more further preferably 6.0% by mass or more, and is preferably 30% by mass or less, more preferably 20% by mass or less, and further preferably 15% by mass or less.

In the case where the component (A) contains a nonionic surfactant, the content of the nonionic surfactant in the cosmetic hair preparation stock solution is preferably 0.05% by mass or more, more preferably 0.10% by mass or more, and further preferably 0.20% by mass or more, and is preferably 10% by mass or less, more preferably 5.0% by mass or less, and further preferably 3.0% by mass or less.

<Component (B): Organic Acid Other than Citric Acid, or Salt Thereof>

The cosmetic hair preparation stock solution constituting the cosmetic hair preparation of the present invention contains an organic acid except for citric acid, or a salt thereof as a component (B). The component (B) is used as an active ingredient for the hair reformation, for example, imparting the bounce and resilience of the hair and suppressing the wavy form of the hair.

Examples of the organic acid used in the present invention include a carboxylic acid based compound other than citric acid and a sulfonic acid based compound, and one kind or two or more kinds thereof may be used.

Examples of the carboxylic acid based compound include an aliphatic monocarboxylic acid, such as acetic acid and propionic acid; an aromatic monocarboxylic acid, such as benzoic acid; an aliphatic dicarboxylic acid, such as malonic acid, succinic acid, glutaric acid, adipic acid, maleic acid, and fumaric acid; an aromatic dicarboxylic acid, such as phthalic acid and isophthalic acid; a polycarboxylic acid, such as polyglutamic acid; a hydroxycarboxylic acid other than citric acid, such as glycolic acid, lactic acid, hydroxyacrylic acid, glyceric acid, malic acid, and tartaric acid; and an acidic amino acid, such as glutamic acid and asparaginic acid. Among these, one or more kind selected from the group consisting of an aliphatic dicarboxylic acid and a hydroxycarboxylic acid is preferred from the standpoint of the enhancement of the hair reformation effect and the standpoint of the solubility in the cosmetic hair preparation stock solution, and a hydroxycarboxylic acid is more preferred from the standpoint of the effect of imparting the bounce and resilience to the hair.

Examples of the sulfonic acid based compound include an aliphatic sulfonic acid, such as methanesulfonic acid and ethanesulfonic acid; and an aromatic sulfonic acid, such as p-toluenesulfonic acid. Among these, an aromatic sulfonic acid is preferred from the standpoint of the enhancement of the hair reformation effect (suppression of the wavy form of the hair) and the standpoint of the solubility in the cosmetic hair preparation stock solution.

The salt in the organic acid salt is preferably an alkali metal salt, more preferably one kind selected from the group consisting of a sodium salt and a potassium salt, and further preferably a sodium salt, from the standpoint of the use as a cosmetic hair preparation and the standpoint of the availability.

Among the above, the component (B) is more preferably one or more kind selected from the group consisting of an aliphatic dicarboxylic acid, a hydroxycarboxylic acid, an aromatic sulfonic acid, and salts thereof, further preferably one or more kind selected from the group consisting of an aliphatic dicarboxylic acid, a hydroxymonocarboxylic acid, a hydroxydicarboxylic acid, an aromatic sulfonic acid, and salts thereof, and still further preferably one or more kind selected from the group consisting of an aliphatic dicarboxylic acid, a hydroxymonocarboxylic acid, a hydroxydicarboxylic acid, and an aromatic sulfonic acid, from the standpoint of the enhancement of the hair reformation effect and the standpoint of the solubility in the cosmetic hair preparation stock solution. The component (B) is preferably a hydroxycarboxylic acid, and more preferably one or more kind selected from the group consisting of a hydroxymonocarboxylic acid and a hydroxydicarboxylic acid, from the standpoint of the enhancement of the effect of imparting the bounce and resilience to the hair. One or more kind selected from the group consisting of an aliphatic dicarboxylic acid and an aromatic sulfonic acid is preferred from the standpoint of the enhancement of the effect of suppressing the wavy form of the hair.

The hydroxycarboxylic acid is more preferably one or more kind selected from the group consisting of lactic acid, malic acid, and tartaric acid, and further preferably malic acid, from the standpoint of the enhancement of the effect of imparting the bounce and resilience to the hair. The aliphatic dicarboxylic acid is more preferably succinic acid from the standpoint of the enhancement of the effect of suppressing the wavy form of the hair, and the aromatic sulfonic acid is preferably p-toluenesulfonic acid from the standpoint of the enhancement of the effect of suppressing the wavy form of the hair.

The component (B) preferably contains an aliphatic dicarboxylic acid and an aromatic sulfonic acid, and more preferably contains succinic acid and p-toluenesulfonic acid, from the standpoint of the enhancement of the effect of suppressing the wavy form of the hair.

The content of the component (B) in the cosmetic hair preparation stock solution is preferably 0.1% by mass or more, more preferably 0.2% by mass or more, and further preferably 0.3% by mass or more, from the standpoint of the enhancement of the hair reformation effect, and is preferably 20% by mass or less, more preferably 15% by mass or less, further preferably 10% by mass or less, and still further preferably 5.0% by mass or less, from the standpoint of the solubility in the cosmetic hair preparation stock solution. The specific range of the content of the component (B) in the cosmetic hair preparation stock solution is preferably 0.1 to 20% by mass, more preferably 0.2 to 15% by mass, further preferably 0.3 to 10% by mass, and still further preferably 0.3 to 5.0% by mass.

In the case where the component (B) is a hydroxycarboxylic acid (preferably one or more kind selected from the group consisting of a hydroxymonocarboxylic acid and a hydroxydicarboxylic acid, more preferably one or more kind selected from the group consisting of glycolic acid, lactic acid, hydroxyacrylic acid, glyceric acid, malic acid, and tartaric acid, further preferably one or more kind selected from the group consisting of lactic acid, malic acid, and tartaric acid, and still further preferably malic acid), the content of the hydroxycarboxylic acid in the cosmetic hair preparation stock solution is 0.1% by mass or more, more preferably 0.2% by mass or more, and further preferably 0.3% by mass or more, and is preferably 3.0% by mass or less, more preferably 2.0% by mass or less, further preferably 1.0% by mass or less, and still further preferably 0.8% by mass or less, from the standpoint of the enhancement of the effect of imparting the bounce and resilience to the hair.

In the case where the component (B) contains an aliphatic dicarboxylic acid and an aromatic sulfonic acid (preferably succinic acid and p-toluenesulfonic acid), the total content of the aliphatic dicarboxylic acid and the aromatic sulfonic acid in the cosmetic hair preparation stock solution is preferably 0.5% by mass or more, more preferably 1.0% by mass or more, further preferably 1.5% by mass or more, and still further preferably 2.0% by mass or more, and is preferably 20% by mass or less, more preferably 15% by mass or less, further preferably 10% by mass or less, and still further preferably 5.0% by mass or less, from the standpoint of the enhancement of the effect of suppressing the wavy form of the hair.

In the case where the component (B) contains an aliphatic dicarboxylic acid and an aromatic sulfonic acid (preferably succinic acid and p-toluenesulfonic acid), the mass ratio of the aliphatic dicarboxylic acid with respect to the aromatic sulfonic acid in the cosmetic hair preparation stock solution is preferably in a range of 1/0.2 to 1/10, and more preferably 1/0.5 to 1/5, from the standpoint of the enhancement of the effect of suppressing the wavy form of the hair.

In the case where an organic acid salt is used as the component (B), the amount of the organic acid salt in the cosmetic hair preparation stock solution converted to the corresponding organic acid is preferably within the aforementioned ranges.

The mass ratio [(B)/(A)] of the component (B) with respect to the component (A) in the cosmetic hair preparation stock solution is preferably 0.005 or more, more preferably 0.01 or more, and further preferably 0.1 or more, from the standpoint of the enhancement of the hair reformation effect, and is preferably 20 or less, more preferably 15 or less, and further preferably 12 or less, from the standpoint of the dischargeability of foam. The specific range of the mass ratio [(B)/(A)] of the component (B) with respect to the component (A) in the cosmetic hair preparation stock solution is preferably 0.005 to 20, more preferably 0.01 to 15, and further preferably 0.1 to 12.

The total content of the component (A) and the component (B) in the cosmetic hair preparation stock solution is preferably 0.15% by mass or more, more preferably 0.3% by mass or more, and further preferably 0.5% by mass or more, from the standpoint of imparting the target capability as the cosmetic hair preparation and the standpoint of the enhancement of the hair reformation effect, and is preferably 40% by mass or less, more preferably 30% by mass or less, and further preferably 20% by mass or less, from the standpoint of the dischargeability of foam. The specific range of the total content of the component (A) and the component (B) in the cosmetic hair preparation stock solution is preferably 0.15 to 40% by mass, more preferably 0.3 to 30% by mass, and further preferably 0.5 to 20% by mass.

<Aqueous Medium>

The cosmetic hair preparation stock solution generally contains an aqueous medium from the standpoint of dissolving or dispersing the component (A), the component (B), and the other additional components. Examples of the aqueous medium include water and an organic solvent. Examples of the organic solvent include a lower alcohol, such as ethanol and isopropyl alcohol; and a low molecular weight diol or triol having 6 or less carbon atoms, such as 1,3-butylene glycol, glycerin, ethylene glycol, propylene glycol, and dipropylene glycol. Among these, water is preferred as the aqueous medium.

The content of the aqueous medium in the cosmetic hair preparation stock solution is preferably 60% by mass or more, and more preferably 70% by mass or more, and is preferably 99.85% by mass or less, and more preferably 99% by mass or less, from the standpoint of dissolving or dispersing the component (A), the component (B), and the other additional components, and the standpoint of the enhancement of the dischargeability of foam and the quality of foam. The specific range of the content of the aqueous medium in the cosmetic hair preparation stock solution is preferably 60 to 99.85% by mass, and more preferably 70 to 99% by mass.

<Component (D): Polymer>

The cosmetic hair preparation stock solution constituting the cosmetic hair preparation of the present invention preferably contains a polymer as a component (D) from the standpoint of the enhancement of the dischargeability of foam and the quality of foam. Examples of the polymer include an anionic polymer, a cationic polymer, a nonionic polymer, and an amphoteric polymer, and one kind or two or more kinds thereof may be used. The polymer used as the component (D) is preferably a water soluble polymer from the standpoint of the solubility in the cosmetic hair preparation stock solution.

The polymer is preferably one or more kind selected from the group consisting of an anionic polymer and a nonionic polymer, and more preferably a nonionic polymer, from the standpoint of the enhancement of the dischargeability of foam through aerosol effect and the quality of foam, and the standpoint of the storage stability.

The weight average molecular weight (Mw) of the component (D) is preferably 10,000 or more, more preferably 50,000 or more, further preferably 100,000 or more, still further preferably 200,000 or more, still more further preferably 500,000 or more, and still more further preferably 1,000,000 or more, from the standpoint of the enhancement of the dischargeability of foam and the quality of foam. The weight average molecular weight thereof is preferably 5,000,000 or less, more preferably 4,000,000 or less, and further preferably 3,500,000 or less, from the standpoint of the storage stability. The specific range of the weight average molecular weight of the component (D) is preferably 10,000 to 5,000,000, more preferably 50,000 to 5,000,000, further preferably 100,000 to 4,000,000, still further preferably 200,000 to 4,000,000, still more further preferably 500,000 to 3,500,000, and still more further preferably 1,000,000 to 3,500,000.

The weight average molecular weight of the component (D) can be measured, for example, by gel permeation chromatography (GPC) under the following condition.

Mobile phase: 50 mM LiBr, (1% $CH_3COOH$/ethanol)/(water)=3/7 (w/w)

Columns: TSKgel α-M (two columns in series) (produced by Tosoh Corporation)

Standard substance: polyethylene glycol

The anionic polymer is preferably a polymer having a carboxy group as an anionic group from the standpoint of the solubility in the cosmetic hair preparation stock solution and the standpoint of the enhancement of the dischargeability of foam and the quality of foam.

Specific examples of the anionic polymer include xanthan gum, a carboxy vinyl polymer, a (meth)acrylic acid-(meth)acrylate ester copolymer, a (meth)acrylic acid-(meth)acrylate ester-alkylacrylamide copolymer, a vinylpyrrolidone-(meth)acrylate ester-(meth)acrylic acid copolymer, a methyl vinyl ether-maleic anhydride monoalkyl ester copolymer, a vinyl acetate-crotonic acid copolymer, a vinyl acetate-crotonic acid-vinyl propionate copolymer, a vinyl acetate-crotonic acid-vinyl neodecanoate copolymer, and a vinyl acetate-maleic acid monoalkyl ester-(meth)acrylate ester copolymer, and one kind or two or more kinds thereof may be used.

Among the above, the anionic polymer is preferably one or more kind selected from the group consisting of xanthan gum, a carboxy vinyl polymer, a (meth)acrylic acid-(meth)acrylate ester copolymer, a (meth)acrylic acid-(meth)acrylate ester-alkylacrylamide copolymer, and a vinylpyrrolidone-(meth)acrylate ester-(meth)acrylic acid copolymer, and more preferably xanthan gum, from the standpoint of the solubility in the cosmetic hair preparation stock solution and the standpoint of the enhancement of the dischargeability of foam and the quality of foam.

Examples of the nonionic polymer include a water soluble polysaccharide, such as starch, cellulose, guar gum, tara gum, locust bean gum, and glucomannan; a hydroxyalkylated water soluble polysaccharide, such as hydroxyethyl cellulose and hydroxypropyl cellulose; a high polymerization-degree polyalkylene glycol compound, such as a high polymerization-degree polyethylene glycol and a high polymerization degree polyethylene glycol-polypropylene glycol copolymer; and a polyvinyl alcohol, and one kind or two or more kinds thereof may be used. The "high polymerization-degree" referred herein preferably means that the weight average molecular weight thereof is in the aforementioned range.

Among the above, the nonionic polymer is preferably one or more kind selected form the group consisting of a water soluble polysaccharide, a hydroxyalkylated water soluble polysaccharide, and a high polymerization-degree polyalkylene glycol compound, more preferably one or more kind selected form the group consisting of starch, cellulose, guar gum, tara gum, locust bean gum, glucomannan, hydroxyethyl cellulose, hydroxypropyl cellulose, a high polymerization-degree polyethylene glycol, and a high polymerization-degree polyethylene glycol-polypropylene glycol copolymer, further preferably one or more kind selected form the group consisting of hydroxyethyl cellulose, hydroxypropyl cellulose, a high polymerization-degree polyethylene glycol, and a high polymerization-degree polyethylene glycol-polypropylene glycol copolymer, and still further preferably one or more kind selected form the group consisting of hydroxyethyl cellulose and a high polymerization-degree polyethylene glycol, from the standpoint of the solubility in the cosmetic hair preparation stock solution and the standpoint of the enhancement of the dischargeability of foam and the quality of foam.

In the case where the component (D) is used, the content of the component (D) in the cosmetic hair preparation stock solution is preferably 0.005% by mass or more, more preferably 0.01% by mass or more, further preferably 0.02% by mass or more, still further preferably 0.05% by mass or more, and still more further preferably 0.1% by mass or more, from the standpoint of the enhancement of the dischargeability of foam and the quality of foam. The content thereof is preferably 5% by mass or less, more preferably 2% by mass or less, further preferably 1% by mass or less, and still further preferably 0.5% by mass or less, from the standpoint of regulating the cosmetic hair preparation stock solution to have a suitable viscosity and the standpoint of the storage stability. The specific range of the content of the component (D) in the cosmetic hair preparation stock solution is preferably 0.005 to 5% by mass, more preferably 0.01 to 2% by mass, further preferably 0.02 to 1% by mass, still further preferably 0.02 to 0.5% by mass, still more further preferably 0.05 to 0.5% by mass, and still more further preferably 0.1 to 0.5% by mass.

In the case where the component (D) is used, the mass ratio [(D)/(A)] of the component (D) with respect to the component (A) in the cosmetic hair preparation stock solution is preferably 0.001 or more, and more preferably 0.002 or more, from the standpoint of the enhancement of the dischargeability of foam and the quality of foam, and is preferably 5 or less, more preferably 3 or less, and further preferably 2 or less, from the standpoint of regulating the cosmetic hair preparation stock solution to have a suitable viscosity and the standpoint of the storage stability. The specific range of the mass ratio [(D)/(A)] of the component (D) with respect to the component (A) in the cosmetic hair preparation stock solution is preferably 0.001 to 5, more preferably 0.001 to 3, and further preferably 0.002 to 2.

<Additional Components>

The cosmetic hair preparation stock solution may appropriately contain additional components in such a range that does not impair the object of the present invention. Examples of the components include components that have been generally mixed in cosmetic hair preparations and the like, for example, an antioxidant, an oil, an antidandruff agent, a vitamin agent, an antimicrobial agent, an anti-inflammatory agent, an antiseptic agent, a chelating agent, a moisturizing agent, a pearlescent agent, a ceramide compound, a perfume, an ultraviolet ray absorbent, and a pH modifier.

The production method of the cosmetic hair preparation stock solution is not particularly limited, and the cosmetic hair preparation stock solution can be produced by blending and mixing the component (A), the component (B), and the other additional components used depending on necessity, by an ordinary method.

<Component (C): Propellant>

The propellant (C) constituting the cosmetic hair preparation of the present invention contains carbon dioxide. The component (C) that contains carbon dioxide enables discharge of fine dense foam, and simultaneously facilitates the penetration of the organic acid as the component (B) into the inside of the hair, enabling the enhancement of the hair reformation effect through the functional mechanism described above.

The content of carbon dioxide in the propellant (C) is preferably 50% by mass or more, more preferably 70% by mass or more, further preferably 80% by mass or more, still further preferably 90% by mass or more, and still more further preferably 100% by mass, from the standpoint of the enhancement of the dischargeability of foam and the quality of foam and the standpoint of facilitating the penetration of the organic acid into the inside of the hair to enhance the hair reformation effect. Accordingly, it is preferred that the propellant (C) is formed only of carbon dioxide.

The component (C) may contain a liquified gas, such as nitrogen, propane, n-butane, isobutane, a liquefied petroleum gas (LPG) as a mixture of these compounds, dimethyl ether, and isopentane, as a propellant other than carbon dioxide, in such a range that does not impair the effects of the present invention.

The charge amount of the propellant (C) in the aerosol type cosmetic hair preparation of the present invention assuming that the total amount of the cosmetic hair preparation stock solution and the propellant (C) is 100% by mass is preferably 0.5% by mass or more, and more preferably 1% by mass or more, and is preferably 5% by mass or less, and more preferably 3% by mass or less, from the standpoint of the enhancement of the dischargeability of foam and the quality of foam, the standpoint of facilitating the penetration of the organic acid into the inside of the hair to enhance the hair reformation effect, and the standpoint of the achievement of a suitable discharge velocity. The specific range of the charge amount of the propellant (C) assuming that the total amount of the cosmetic hair preparation stock solution and the propellant (C) is 100% by mass is preferably 0.5 to 5% by mass, and more preferably 1 to 3% by mass.

The inner pressure of the aerosol container after charging the propellant (C) at 25° C. is regulated preferably to 0.1 MPa or more, and more preferably to 0.3 MPa or more, and is regulated preferably to 1.3 MPa or less, and more preferably to 1.0 MPa or less, for the achievement of a suitable discharge velocity. The specific range of the inner pressure of the aerosol container after charging the propellant (C) is preferably 0.1 to 1.3 MPa, and more preferably 0.3 to 1.0 MPa.

<Aerosol Container>

The aerosol type cosmetic hair preparation of the present invention is used after charging in an aerosol container. Examples of the aerosol container used include a known pressure resistant container, such as a metal container and a resin container, and a double structure container including a pressure resistant container having an inner bag housed therein. In the double structure container, it is preferred that the cosmetic hair preparation stock solution is housed in the inner bag, and the propellant (C) is charged between the pressure resistant container and the inner bag.

The preparation method of the aerosol type cosmetic hair preparation of the present invention is not particularly limited. For example, the aerosol type cosmetic hair preparation can be prepared in such a manner that the cosmetic hair preparation stock solution is charged in the pressure resistant container constituting the aerosol container, followed by attaching a valve thereto, and then the propellant (C) is charged through the valve.

<Use Method of Aerosol Type Cosmetic Hair Preparation>

The use method of the aerosol type cosmetic hair preparation of the present invention is not particularly limited, as far as the method includes steps of discharging the cosmetic hair preparation in the form of foam from an aerosol container, and applying to the hair.

The cosmetic hair preparation discharged in the form of foam may be applied to the dried hair or may be applied to the wet hair depending on the kind of the cosmetic hair preparation.

For example, in the case where the cosmetic hair preparation of the present invention is a hair cleansing agent, examples of the use method include a method including steps of applying the cosmetic hair preparation discharged in the form of foam to the hair, and cleansing the hair. The step of cleansing the hair may include an operation of foaming the hair cleansing agent on the hair and then an operation of rinsing out the hair cleansing agent.

In the case where the cosmetic hair preparation of the present invention is a hair conditioning agent or a hair treatment agent, examples of the use method include a method including steps of applying and adapting the cosmetic hair preparation discharged in the form of foam from the aerosol container to the hair in a wet state or a dry state after cleansing, and then rinsing out depending on necessity.

The cosmetic hair preparation of the present invention discharged in the form of foam contains carbon dioxide gas, can be uniformly spread over the entire hair with good applicability, and can be sufficiently adapted to the hair. Therefore, the use of the cosmetic hair preparation of the present invention onto the hair, for example, by the aforementioned method can allow the active ingredient, such as the organic acid, to penetrate easily into the inside of the hair.

The amount of the cosmetic hair preparation applied to the hair in terms of mass ratio with respect to the mass of the hair (mass of cosmetic hair preparation/mass of hair) is preferably 0.002 or more, and more preferably 0.003 or more, and is preferably 0.6 or less, and more preferably 0.5 or less. The hair to be the object of treatment may be at least a part of the head hair.

<Reformation Method of Hair and Use>

The present invention can provide a reformation method of the hair including a step of applying the aerosol type cosmetic hair preparation to the hair.

The present invention can also provide a method of allowing an organic acid to penetrate into the inside of the hair, including a step of applying an aerosol type cosmetic hair preparation containing a cosmetic hair preparation stock solution containing a surfactant (A) and an organic acid or a salt thereof (B1), and a propellant (C) containing carbon dioxide, having a pH at 20° C. of 3.0 or more and 5.0 or less, preferably the aforementioned aerosol type cosmetic hair preparation, to the hair.

The present invention can further provide use of an aerosol type cosmetic hair preparation containing a cosmetic hair preparation stock solution containing a surfactant (A) and an organic acid or a salt thereof (B1), and a propellant (C) containing carbon dioxide, having a pH at 20° C. of 3.0 or more and 5.0 or less, preferably the aforementioned aerosol type cosmetic hair preparation, for hair reformation.

It suffices that the method and the use described above each include a step of discharging an aerosol type cosmetic hair preparation containing a cosmetic hair preparation stock solution containing a surfactant (A) and an organic acid or a salt thereof (B1), and a propellant (C) containing carbon dioxide, having a pH at 20° C. of 3.0 or more and 5.0 or less, preferably discharging the cosmetic hair preparation from the aerosol container of the aerosol type cosmetic hair preparation of the present invention, in the form of foam from an aerosol container, and applying to the hair by coating or the like. According to the configuration, the organic acid, which is the active ingredient for the hair reformation, can be easily allowed to penetrate into the inside of the hair, and thereby the hair reformation effect, for example, imparting the bounce and resilience of the hair and suppressing the wavy form of the hair, can be imparted.

The cosmetic hair preparation discharged in the form of foam may be applied to the dried hair or may be applied to the wet hair depending on the kind of the cosmetic hair preparation.

The applying method of the cosmetic hair preparation to the hair, the amount of the cosmetic hair preparation applied to the hair, and the preferred embodiments thereof are the same as described above. The organic acid or a salt thereof (B1) is the same as the component (B) except that citric acid and a salt thereof may be included therein.

In relation to the aforementioned embodiments, the present invention further discloses the following embodiments.

<1>

An aerosol type cosmetic hair preparation containing a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less.

<2>

The aerosol type cosmetic hair preparation according to the item <1>, wherein the component (A) contains one or more kind selected from the group consisting of an anionic surfactant and a nonionic surfactant.

<3>

The aerosol type cosmetic hair preparation according to the item <2>, wherein the anionic surfactant is one or more kind selected from the group consisting of an alkylbenzene sulfonate salt, an alkyl or alkenyl ether sulfate salt, an alkyl or alkenyl sulfate salt, an alkyl sulfonate salt, a saturated or unsaturated fatty acid salt, an alkyl or alkenyl ether carboxylate salt, an α-sulfo fatty acid salt, an N-acylamino acid salt, a phosphoric acid mono- or diester salt, and a sulfosuccinic acid ester salt, preferably one or more kind selected from the group consisting of an alkyl sulfate salt, an alkyl ether sulfate salt, an alkyl ether carboxylate salt, and an N-acylamino acid salt, more preferably one or more kind selected from the group consisting of an alkyl ether sulfate salt and an N-acylamino acid salt, and further preferably one or more kind selected from the group consisting of sodium laureth sulfate, ammonium laureth sulfate, and sodium cocoyl glutamate.

<4>

The aerosol type cosmetic hair preparation according to the item <2> or <3>, wherein the nonionic surfactant is one or more kind selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, a higher fatty acid sucrose ester, a polyglycerin fatty acid ester, a polyoxyalkylene hydrogenated castor oil, and an alkylsaccharide, preferably one or more kind selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, and a polyoxyalkylene hydrogenated castor oil, more preferably one or more kind selected from the group consisting of a polyoxyalkylene alkyl ether, an alkyl glucoside, an alkyl alkanolamide, an alkyl glyceryl ether, and a polyoxyalkylene hydrogenated castor oil, and further preferably a polyoxyalkylene hydrogenated castor oil.

<5>

The aerosol type cosmetic hair preparation according to any one of the items <1> to <4>, wherein the content of the component (A) in the cosmetic hair preparation stock solution is preferably 0.05 to 30% by mass, more preferably 0.10 to 20% by mass, and further preferably 0.20 to 15% by mass.

<6>

The aerosol type cosmetic hair preparation according to any one of the items <2> to <5>, wherein the content of the anionic surfactant in the cosmetic hair preparation stock solution is preferably 0.50% by mass or more, more preferably 1.0% by mass or more, further preferably 3.0% by mass or more, still further preferably 5.0% by mass or more, and still more further preferably 6.0% by mass or more, and is preferably 30% by mass or less, more preferably 20% by mass or less, and further preferably 15% by mass or less.

<7>

The aerosol type cosmetic hair preparation according to any one of the items <2> to <6>, wherein the content of the nonionic surfactant in the cosmetic hair preparation stock solution is preferably 0.05% by mass or more, more preferably 0.10% by mass or more, and further preferably 0.20% by mass or more, and is preferably 10% by mass or less, more preferably 5.0% by mass or less, and further preferably 3.0% by mass or less.

<8>

The aerosol type cosmetic hair preparation according to any one of the items <1> to <7>, wherein the component (B) is one or more kind selected from the group consisting of a carboxylic acid based compound other than citric acid and a sulfonic acid based compound, preferably one or more kind selected from the group consisting of an aliphatic dicarboxylic acid, a hydroxycarboxylic acid, an aromatic sulfonic acid, and salts thereof, more preferably one or more kind selected from the group consisting of an aliphatic dicarboxylic acid, a hydroxymonocarboxylic acid, a hydroxydicarboxylic acid, an aromatic sulfonic acid, and salts thereof, and still further preferably one or more kind selected from the group consisting of an aliphatic dicarboxylic acid, a hydroxymonocarboxylic acid, a hydroxydicarboxylic acid, and an aromatic sulfonic acid.

<9>

The aerosol type cosmetic hair preparation according to the item <8>, wherein the aliphatic dicarboxylic acid is one or more kind selected from the group consisting of malonic acid, succinic acid, glutaric acid, adipic acid, maleic acid, and fumaric acid, and preferably succinic acid.

<10>

The aerosol type cosmetic hair preparation according to the item <8> or <9>, wherein the hydroxycarboxylic acid is one or more kind selected from the group consisting of a hydroxymonocarboxylic acid and a hydroxydicarboxylic acid, preferably one or more kind selected from the group consisting of glycolic acid, lactic acid, hydroxyacrylic acid, glyceric acid, malic acid, and tartaric acid, more preferably one or more kind selected from the group consisting of lactic acid, malic acid, and tartaric acid, and further preferably malic acid.

<11>

The aerosol type cosmetic hair preparation according to any one of the items <8> to <10>, wherein the aromatic sulfonic acid is p-toluenesulfonic acid.

<12>

The aerosol type cosmetic hair preparation according to any one of the items <1> to <11>, wherein the component (B) contains an aliphatic dicarboxylic acid and an aromatic sulfonic acid, and preferably contains succinic acid and p-toluenesulfonic acid.

<13>

The aerosol type cosmetic hair preparation according to any one of the items <1> to <12>, wherein the content of the component (B) in the cosmetic hair preparation stock solution is preferably 0.1 to 20% by mass, more preferably 0.2 to 15% by mass, further preferably 0.3 to 10% by mass, and still further preferably 0.3 to 5.0% by mass.

<14>

The aerosol type cosmetic hair preparation according to any one of the items <8> to <13>, wherein the content of the hydroxycarboxylic acid in the cosmetic hair preparation stock solution is 0.1% by mass or more, more preferably 0.2% by mass or more, and further preferably 0.3% by mass or more, and is preferably 3.0% by mass or less, more preferably 2.0% by mass or less, further preferably 1.0% by mass or less, and still further preferably 0.8% by mass or less.

<15>

The aerosol type cosmetic hair preparation according to any one of the items <8> to <14>, wherein the total content of the aliphatic dicarboxylic acid and the aromatic sulfonic acid in the cosmetic hair preparation stock solution is preferably 0.5% by mass or more, more preferably 1.0% by mass or more, further preferably 1.5% by mass or more, and still further preferably 2.0% by mass or more, and is preferably 20% by mass or less, more preferably 15% by mass or less, further preferably 10% by mass or less, and still further preferably 5.0% by mass or less.

<16>

The aerosol type cosmetic hair preparation according to any one of the items <8> to <15>, wherein the mass ratio of the aliphatic dicarboxylic acid with respect to the aromatic sulfonic acid in the cosmetic hair preparation stock solution is preferably in a range of 1/0.2 to 1/10, and more preferably 1/0.5 to 1/5.

<17>

The aerosol type cosmetic hair preparation according to any one of the items <1> to <16>, wherein the mass ratio [(B)/(A)] of the component (B) with respect to the component (A) in the cosmetic hair preparation stock solution is preferably 0.15 to 40% by mass, more preferably 0.3 to 30% by mass, and further preferably 0.5 to 20% by mass.

<18>

The aerosol type cosmetic hair preparation according to any one of the items <1> to <17>, wherein the total content of the component (A) and the component (B) in the cosmetic hair preparation stock solution is preferably 0.15 to 40% by mass, more preferably 0.3 to 30% by mass, and further preferably 0.5 to 20% by mass.

<19>

The aerosol type cosmetic hair preparation according to any one of the items <1> to <18>, wherein the cosmetic hair preparation stock solution contains an aqueous medium in an amount of preferably 60 to 99.85% by mass, and more preferably 70 to 99% by mass.

<20>

The aerosol type cosmetic hair preparation according to the item <19>, wherein the aqueous medium is one or more kind selected from the group consisting of water, a lower alcohol, and a low molecular weight diol or triol having 6 or less carbon atoms, preferably one or more kind selected from the group consisting of water, ethanol, isopropyl alcohol, 1,3-butylene glycol, glycerin, ethylene glycol, propylene glycol, and dipropylene glycol, and more preferably water.

<21>

The aerosol type cosmetic hair preparation according to any one of the items <1> to <20>, wherein the cosmetic hair preparation stock solution further contains a polymer, preferably one or more kind selected from the group consisting of an anionic polymer and a nonionic polymer, and more preferably a nonionic polymer, as a component (D).

<22>

The aerosol type cosmetic hair preparation according to the item <21>, wherein the nonionic polymer is one or more kind selected from the group consisting of a water soluble polysaccharide, a hydroxyalkylated water soluble polysaccharide, and a high polymerization-degree polyalkylene glycol compound, more preferably one or more kind selected from the group consisting of starch, cellulose, guar gum, tara gum, locust bean gum, glucomannan, hydroxyethyl cellulose, hydroxypropyl cellulose, a high polymerization-degree polyethylene glycol, and a high polymerization-degree polyethylene glycol-polypropylene glycol copolymer, further preferably one or more kind selected from the group consisting of hydroxyethyl cellulose, hydroxypropyl cellulose, a high polymerization-degree polyethylene glycol, and a high polymerization-degree polyethylene glycol-polypropylene glycol copolymer, and still further preferably one or more kind selected from the group consisting of hydroxyethyl cellulose and a high polymerization-degree polyethylene glycol.

<23>

The aerosol type cosmetic hair preparation according to the item <21> or <22>, wherein the content of the component (D) in the cosmetic hair preparation stock solution is preferably 0.005 to 5% by mass, more preferably 0.01 to 2% by mass, further preferably 0.02 to 1% by mass, still further preferably 0.02 to 0.5% by mass, still more further preferably 0.05 to 0.5% by mass, and still more further preferably 0.1 to 0.5% by mass.

<24>

The aerosol type cosmetic hair preparation according to any one of the items <21> to <23>, wherein the mass ratio [(D)/(A)] of the component (D) with respect to the component (A) in the cosmetic hair preparation stock solution is preferably 0.001 to 5, more preferably 0.001 to 3, and further preferably 0.002 to 2.

<25>

The aerosol type cosmetic hair preparation according to any one of the items <1> to <24>, wherein the content of carbon dioxide in the propellant (C) is preferably 50% by mass or more, more preferably 70% by mass or more, further preferably 80% by mass or more, still further preferably 90% by mass or more, and still more further preferably 100% by mass.

<26>

The aerosol type cosmetic hair preparation according to any one of the items <1> to <25>, wherein the charge amount of the propellant (C) in the aerosol type cosmetic hair preparation assuming that the total amount of the cosmetic hair preparation stock solution and the propellant (C) is 100% by mass is preferably 0.5 to 5% by mass, and more preferably 1 to 3% by mass.

<27>

The aerosol type cosmetic hair preparation according to any one of the items <1> to <26>, wherein the pH of the cosmetic hair preparation at 20° C. is preferably 3.0 to 4.8, more preferably 3.0 to 4.5, further preferably 3.0 to 4.2, still further preferably 3.2 to 4.2, and still more further preferably 3.4 to 4.2.

<28>

The aerosol type cosmetic hair preparation according to any one of the items <1> to <27>, wherein the aerosol type cosmetic hair preparation is an aerosol type hair cleansing agent, a hair conditioning agent, a hair treatment agent, a hair styling agent, a hair dye, or a hair growth agent, and preferably an aerosol type hair cleansing agent.

<29>

A use method of the aerosol type cosmetic hair preparation according to any one of the items <1> to <28>, including steps of discharging the cosmetic hair preparation in the form of foam from an aerosol container, and applying to the hair.

<30>

A reformation method of the hair including a step of applying the aerosol type cosmetic hair preparation according to any one of the items <1> to <28> to the hair.

<31>

Use of an aerosol type cosmetic hair preparation containing a cosmetic hair preparation stock solution containing a surfactant (A) and an organic acid or a salt thereof (B1), and a propellant (C) containing carbon dioxide, having a pH at 20° C. of 3.0 or more and 5.0 or less, preferably the aerosol type cosmetic hair preparation according to any one of the items <1> to <28>, for hair reformation.

<32>

A method of allowing an organic acid to penetrate into the inside of the hair, including a step of applying an aerosol type cosmetic hair preparation containing a cosmetic hair preparation stock solution containing a surfactant (A) and an organic acid or a salt thereof (B1), and a propellant (C) containing carbon dioxide, having a pH at 20° C. of 3.0 or more and 5.0 or less, preferably the aerosol type cosmetic hair preparation according to any one of the items <1> to <28>, to the hair.

EXAMPLES

The present invention will be described with reference to examples below, but the present invention is not limited to the range of the examples. In the examples, the pH was measured according to the following method.

(pH)

The pH at 20° C. of the aerosol type hair cleansing agent containing the propellant (or the hair cleansing agent stock solution for the case containing no propellant) was measured in such a manner that the hair cleansing agent or the hair cleansing agent stock solution discharged from the aerosol container was diluted 20 times with water and well agitated to prepare an aqueous solution, which was measured with a pH meter (HM-30R, produced by DKK-TOA Corporation).

Examples 1 to 6 and Comparative Examples 1 to 12

(Production and Evaluation of Hair Cleansing Agents)

The components to be blended in the hair cleansing agent stock solution were blended according to each of the compositions shown in Tables 1 to 3, and then mixed until uniform, so as to prepare a hair cleansing agent stock solution. Subsequently, for the case containing a propellant, 50 g of the hair cleansing agent stock solution and the propellant shown in the tables were charged to make the mass ratio shown in the tables in an aerosol container having a capacity of 100 mL (container type: BL35A115-H, produced by Toyo Seikan Kaisha, Ltd., inner coating: epoxy phenol type, outer surface: silver solid color (or white)), so as to produce an aerosol type hair cleansing agent. The inner pressure of the aerosol container after charging the propellant was regulated to a range of 0.65 to 0.85 MPa.

The hair cleansing agents thus produced were evaluated in the following manner. The results are shown in Tables 1 to 3.

The blended amounts shown in the tables each were the active ingredient amount (% by mass) except for hydrochloric acid.

<Increment Rate of Flexural Elastic Modulus of Hair>

The hair cleansing agents shown in Table 1 were measured for the increment rate of the flexural elastic modulus of the hair according to the following method for evaluating the hair reformation effect (imparting the bounce and resilience to the hair).

The hair used was a Japanese female hair bundle having been treated with a bleach agent four times. 20 threads of the hair were randomly picked out therefrom for each of the untreated hair and the hair to be treated. The hair specimens were immersed in ion exchanged water for 10 minutes, and then immersed in a 10% aqueous solution of a plain shampoo having the following composition for 60 seconds. Subsequently, the hair samples were rinsed with ion exchanged water for 90 seconds, and then spontaneously dried under condition of a temperature of 20° C. and a humidity of 65%, so as to prepare two hair specimens. One of the hair samples was designated as the untreated hair, and the other sample was subjected to the following hair treatment.

[Composition of Plain Shampoo]

| Component | (% by mass) |
|---|---|
| Sodium polyoxyethylene (2) lauryl ether sulfate (*1) | 15.5 |
| Lauric acid diethanolamide (*2) | 1.5 |
| Tetrasodium edetate | 0.3 |
| Sodium benzoate | 1.43 |
| Purified water | balance |
| Total | 100.0 |

(*1): 57.4% by mass as Emal 227 (produced by Kao Corporation, active ingredient: 27% by mass)
(*2): Aminon L-02 (produced by Kao Corporation)

(Hair Treatment)

The hair cleansing agent shown in Table 1 was discharged from the aerosol container (for the case containing no propellant, the hair cleansing agent stock solution was used), and diluted 10 times with water (used in an amount of 3.0 g in total), in which the hair sample was immersed under room temperature condition for 15 minutes to perform the hair treatment. After completing the treatment, the hair specimen was rinsed with ion exchanged water for 90 seconds, and then spontaneously dried under condition of a temperature of 20° C. and a humidity of 65%, so as to prepare the treated hair.

(Measurement of Flexural Elastic Modulus)

The untreated hair and the treated hair each were measured for the flexural elastic modulus. The flexural elastic modulus was measured with a hair flexural elasticity testing system (FBS900, produced by Keystone Scientific K.K.) under condition of a temperature of 20° C. and a humidity of 65% with the following conditions. 20 threads of hair were measured for each of the untreated hair and the treated hair.

[Measurement Condition]

Proportion gain: 25
Integrate gain: 2
Derivative gain: 50
Fiber width: 1
Sample interval: 200 mS
Deflection (mm): 0.1
Offset move (mm): 0.5
Maximum force (mg): 400
Gauge force (mg): 2
Repear cycle: 1
Rate (mm/sec): 0.01
Start angle: 0
Rotation angle: 0
End angle: 0
Relaxation time: 0
Bend analysis option
Start analysis at: 0 Microns deflection
End analysis at: 100 Microns deflection
Analysis angle: 0 Degrees
Cantilever length: 2250 Microns The increment rate (%) of the flexural elastic modulus of the hair was calculated by (flexural elastic modulus of treated hair)/(flexural elastic modulus of untreated hair)×100(%). The results are shown in Table 1.

A higher increment rate of the flexural elastic modulus of the hair means a higher hair modification effect (improvement of hair bounce and elasticity).

For the increment rate of the flexural elastic modulus, the values of the flexural elastic modulus of the untreated hair and the treated hair were statistically processed and evaluated based on the statistical significance level according to the following standard. The results are shown in Table 1. The grades A and B mean that a significant hair modification effect (improvement of hair bounce and elasticity) is obtained.

A: Significant difference at a statistical significance level of 0.01 or less
B: Statistical significance levels above 0.01 and below 0.05 are significantly different
C: No statistically significant difference <Increment Rate of Stress Relaxation Rate of Hair>

The hair cleansing agents shown in Tables 2 and 3 were measured for the increment rate of the stress relaxation rate of the hair according to the following method for evaluating the hair modification effect (improvement of hair waviness).

The hair used was a Japanese female untreated hair bundle. 20 threads of the hair were randomly picked out therefrom for each of the untreated specimen and the specimen to be treated. The samples were immersed in a 10% aqueous solution of the plain shampoo having the aforementioned composition for 60 seconds, and then spontaneously dried under condition of a temperature of 20° C. and a humidity of 65%.

Subsequently, one of the hair samples (untreated samples) was immersed in ion exchanged water under room temperature condition for 15 minutes, and then dried under condition of a temperature of 20° C. and a humidity of 65% for 48 hours to prepare the untreated hair.

For the other one of the hair samples (treated sample), 3.0 g of the hair cleansing agent shown in Tables 2 and 3 was discharged from the aerosol container (for the case containing no propellant, 3.0 g of the hair cleansing agent stock solution was used), in which the hair was immersed under room temperature condition for 15 minutes to perform the hair treatment. After completing the treatment, the hair specimen was rinsed with ion exchanged water for 90 seconds, and then spontaneously dried under condition of a temperature of 20° C. and a humidity of 65% for 48 hours, so as to prepare the treated hair.

The untreated hair and the treated hair each were applied with a tensile stress under condition of a temperature of 20° C., a humidity of 65%, a tensile speed of 18 mm/min, and a chuck distance of 30 mm with an automatic tensile tester (MTT680, produced by Dia-Stron Ltd.), and a state of 1% tension was retained for 3 minutes. Based on the initial stress value at a tensile state retention time of 0 second, the stress relaxation rate was calculated from the relative stress value after 3 minutes. 10 threads of the hair were measured for each of the untreated hair and the treated hair.

The stress relaxation rates of the untreated hair and the treated hair and the increment rate of the stress relaxation rate before and after the treatment were calculated by the following expressions.

$$\text{Stress relaxation rate (\%)} = (\text{initial stress value } (N) \text{ at tensile state retention time of 0 second} - \text{stress value } (N) \text{ at tensile state retention time of 3 minutes}) / (\text{initial stress value } (N) \text{ at tensile state retention time of 0 second}) \times 100 (\%)$$

$$\text{Increment rate of stress relaxation rate (\%)} = (\text{stress relaxation rate of treated hair} - \text{stress relaxation rate of untreated hair}) / (\text{stress relaxation rate of untreated hair}) \times 100 (\%)$$

For the increment rate of the stress relaxation rate, the values of the stress relaxation rate of the untreated hair and the treated hair were statistically processed and evaluated based on the statistical significance level according to the following standard. The results are shown in Tables 2 and 3. The case where the increment rate of the stress relaxation rate is a positive value, and the evaluation result of the significant difference is A or B means that a significant hair reformation effect (suppression of the wavy form of the hair) is obtained.

A: Significant difference at a statistical significance level of 0.01 or less

B: Statistical significance levels above 0.01 and below 0.05 are significantly different C: No statistically significant difference

TABLE 1

| | | | Example | | Comparative Example | | | | |
|---|---|---|---|---|---|---|---|---|---|
| | | | 1 | 2 | 1 | 2 | 3 | 4 | 5 |
| Composition of hair cleansing agent stock solution (% by mass) | (A) | Na laureth sulfate | | | | | | | |
| | | Ammonium laureth sulfate | | | | | | | |
| | | Na cocoyl glutamate | | | | | | | |
| | | PEG-60 hydrogenated castor oil | 0.30 | 0.30 | 0.30 | 0.30 | | 0.30 | 0.30 |
| | (B) | Succinic acid | | | | | | | |
| | | Malic acid | 0.50 | 0.50 | 0.50 | | 0.50 | 0.50 | 0.50 |
| | | p-Toluenesulfonic acid | | | | | | | |
| | (B') | Hydrochloric acid | | | | 0.02 | | | |
| | (D) | Hydroxyethyl cellulose (Mw: 1,500,000) | 0.40 | 0.40 | 0.40 | 0.40 | 0.40 | | 0.40 |
| | | Polyethylene glycol (Mw: 2,000,000) | | | | | | | |
| | | pH Modifier | proper amount | | | | | | |
| | | Water | balance | | | | | | |
| | | Total | 100.0 | 100.0 | 100.0 | 100.0 | 100.0 | 100.0 | 100.0 |
| | | Content of component (A) (% by mass) | 0.30 | 0.30 | 0.30 | 0.30 | 0.00 | 0.30 | 0.30 |
| | | Content of component (B) (% by mass) | 0.50 | 0.50 | 0.50 | 0.00 | 0.50 | 0.50 | 0.50 |
| | | Total content of components (A) and (B) (% by mass) | 0.80 | 0.80 | 0.80 | 0.30 | 0.50 | 0.80 | 0.80 |
| | | Content of component (D) (% by mass) | 0.40 | 0.40 | 0.40 | 0.40 | 0.40 | 0.00 | 0.40 |
| | | Mass ratio (B)/(A) | 1.67 | 1.67 | 1.67 | 0.00 | — | 1.67 | 1.67 |
| | | Mass ratio (D)/(A) | 1.33 | 1.33 | 1.33 | 1.33 | — | 0.00 | 1.33 |
| Composition of hair cleansing agent (% by mass) | | Hair cleansing agent stock solution | 97.80 | 97.80 | 100.00 | 97.80 | 100.00 | 100.00 | 97.80 |
| | (C) | Carbon dioxide | 2.20 | 2.20 | | 2.20 | | | 2.20 |
| | | Nitrogen | | | | | | | |
| | | LPG | | | | | | | |
| Evaluation result | | pH of hair cleansing agent (20° C.) | 3.00 | 3.40 | 3.00 | 3.00 | 3.00 | 3.00 | 5.40 |
| | | Increment rate of flexural elastic modulus of hair (%) | 4.70 | 6.28 | 1.95 | 0.29 | 1.60 | −1.30 | 1.30 |
| | | Evaluation result of significant difference | A | A | C | C | C | C | C |

TABLE 2

| | | | Example 3 | Comparative Example 6 | Example 4 | Comparative Example 7 | Comparative Example 8 |
|---|---|---|---|---|---|---|---|
| Composition of hair cleansing agent stock solution (% by mass) | (A) | Na laureth sulfate | | | 10.77 | 10.77 | 10.77 |
| | | Ammonium laureth sulfate | | | | | |
| | | Na cocoyl glutamate | | | | | |
| | | PEG-60 hydrogenated castor oil | 0.30 | 0.30 | | | |
| | (B) | Succinic acid | 1.50 | 1.50 | 0.50 | 0.50 | |
| | | Malic acid | | | | | |
| | | p-Toluenesulfonic acid | 2.00 | 2.00 | 2.00 | 2.00 | 2.00 |
| | (B') | Hydrochloric acid | | | | | |
| | (D) | Hydroxyethyl cellulose (Mw: 1,500,000) | 0.40 | 0.40 | 0.40 | 0.40 | 0.40 |
| | | Polyethylene glycol (Mw: 2,000,000) | | | | | |
| | | pH Modifier | proper amount | | | | |
| | | Water | balance | | | | |
| | | Total | 100.0 | 100.0 | 100.0 | 100.0 | 100.0 |
| | | Content of component (A) (% by mass) | 0.30 | 0.30 | 10.77 | 10.77 | 10.77 |
| | | Content of component (B) (% by mass) | 3.50 | 3.50 | 2.50 | 2.50 | 2.00 |
| | | Total content of components (A) and (B) (% by mass) | 3.80 | 3.80 | 13.27 | 13.27 | 12.77 |
| | | Content of component (D) (% by mass) | 0.40 | 0.40 | 0.40 | 0.40 | 0.40 |
| | | Mass ratio (B)/(A) | 11.67 | 11.67 | 0.23 | 0.23 | 0.19 |
| | | Mass ratio (D)/(A) | 1.33 | 1.33 | 0.04 | 0.04 | 0.04 |
| Composition of hair cleansing agent (% by mass) | | Hair cleansing agent stock solution | 97.80 | 100.00 | 97.80 | 100.00 | 97.80 |
| | (C) | Carbon dioxide | 2.20 | | 2.20 | | 2.20 |
| | | Nitrogen | | | | | |
| | | LPG | | | | | |
| Evaluation result | | pH of hair cleansing agent (20° C.) | 3.40 | 3.40 | 3.40 | 3.40 | 5.80 |
| | | Increment rate of stress relaxation rate of hair (%) | 0.48 | 0.40 | 0.38 | 0.31 | 0.30 |
| | | Evaluation result of significant difference | B | C | B | C | C |

TABLE 3

| | | | Example 5 | Comparative Example 9 | Comparative Example 10 | Comparative Example 11 | Example 6 | Comparative Example 12 |
|---|---|---|---|---|---|---|---|---|
| Composition of hair cleansing agent stock solution (% by mass) | (A) | Na laureth sulfate | 10.77 | 10.77 | 10.77 | 10.77 | 10.77 | 10.77 |
| | | Ammonium laureth sulfate | | | | | 1.00 | 1.00 |
| | | Na cocoyl glutamate | | | | | 0.97 | 0.97 |
| | | PEG-60 hydrogenated castor oil | | | | | | |
| | (B) | Succinic acid | 0.50 | 0.50 | 0.50 | 0.50 | 1.50 | 1.50 |
| | | Malic acid | | | | | | |
| | | p-Toluenesulfonic acid | 1.50 | 1.50 | 1.50 | 1.50 | 1.00 | 1.00 |
| | (B') | Hydrochloric acid | | | | | | |
| | (D) | Hydroxyethyl cellulose (Mw: 1,500,000) | 0.40 | 0.40 | 0.40 | 0.40 | | |

TABLE 3-continued

| | | Example | Comparative Example | | | Example | Comparative Example |
|---|---|---|---|---|---|---|---|
| | | 5 | 9 | 10 | 11 | 6 | 12 |
| | Polyethylene glycol (Mw: 2,000,000) | | | | | 0.03 | 0.03 |
| | pH Modifier | proper amount | | | | | |
| | Water | balance | | | | | |
| | Total | 100.0 | 100.0 | 100.0 | 100.0 | 100.0 | 100.0 |
| | Content of component (A) (% by mass) | 10.77 | 10.77 | 10.77 | 10.77 | 12.74 | 12.74 |
| | Content of component (B) (% by mass) | 2.00 | 2.00 | 2.00 | 2.00 | 2.50 | 2.50 |
| | Total content of components (A) and (B) (% by mass) | 12.77 | 12.77 | 12.77 | 12.77 | 15.24 | 15.24 |
| | Content of component (D) (% by mass) | 0.40 | 0.40 | 0.40 | 0.40 | 0.03 | 0.03 |
| | Mass ratio (B)/(A) | 0.19 | 0.19 | 0.19 | 0.19 | 0.20 | 0.20 |
| | Mass ratio (D)/(A) | 0.04 | 0.04 | 0.04 | 0.04 | 0.002 | 0.002 |
| Composition of hair cleansing agent (% by mass) | Hair cleansing agent stock solution | 97.80 | 100.00 | 97.80 | 90.00 | 97.80 | 100.00 |
| | (C) Carbon dioxide | 2.20 | | | | 2.20 | |
| | Nitrogen | | | 2.20 | | | |
| | LPG | | | | 10.00 | | |
| Evaluation result | pH of hair cleansing agent (20° C.) | 3.40 | 3.40 | 3.40 | 3.40 | 4.00 | 4.00 |
| | Increment rate of stress relaxation rate of hair (%) | 0.52 | 0.21 | 0.14 | 0.39 | 1.07 | 0.75 |
| | Evaluation result of significant difference | A | C | C | C | A | C |

The component used in the tables was as follows.

<Surfactant (A)>

[Anionic Surfactant]

Na laureth sulfate: Sodium polyoxyethylene (2) lauryl ether sulfate, "Emal 227", produced by Kao Corporation, active ingredient: 27% by mass Ammonium laureth sulfate: ammonium polyoxyethylene (1) alkyl(C10-16) ether sulfate, "Emal 125A", produced by Kao Corporation, active ingredient: 25% by mass Na cocoyl glutamate: "Amisoft CS-22B", produced by Ajinomoto Healthy Supply Co., Inc., active ingredient: 25% by mass

[Nonionic Surfactant]

PEG-60 hydrogenated castor oil: "Emanon CH-60K", produced by Kao Corporation, active ingredient: 100% by mass <Organic Acid or Salt Thereof (B)>

Succinic acid: produced by Nippon Shokubai Co., Ltd.

Malic acid: 50% liquid malic acid, produced by Kawasaki Kasei Chemicals Ltd.

p-Toluenesulfonic acid: 70% p-toluenesulfonic acid, produced by Konan Chemical Manufacturing Co., Ltd.

<Acid (B') Other than Component (B)>

Hydrochloric acid: 1 mol/L hydrochloric acid, produced by Fujifilm Wako Pure Chemical Corporation <Polymer (D)>

Hydroxyethyl cellulose: "HEC Daicel SE850K", produced by Daicel Finechem, Ltd., weight average molecular weight: 1,500,000

Polyethylene glycol: "Polyox WSR N-60K", produced by Dow Chemical Company, weight average molecular weight: 2,000,000

<pH Modifier>

Liquid caustic potash (48%): produced by Occidental Chemical Corporation (US)

As shown in Table 1, it is understood that the hair applied with the aerosol type hair cleansing agent of the example has a high increment rate of the flexural elastic modulus. As shown in Tables 2 and 3, it is understood that the hair applied with the aerosol type hair cleansing agent of the example enjoys the hair reformation effect by the increase of the stress relaxation rate of the hair. It is considered that these are obtained by the effect of the effective penetration of the component (B) into the inside of the hair.

On the other hand, no significant hair reformation effect is obtained in Comparative Examples 1, 3, 4, 6, 7, and 9 to 12 containing no carbon dioxide as a propellant, Comparative Example 2 containing no component (B), Comparative Example 3 containing no component (A), and Comparative Examples 5 and 8 having a pH outside the scope of the present invention.

(Evaluation of Penetration State of p-Toluenesulfonic Acid)

After sufficiently moistening approximately 10 mg of a Japanese female untreated hair bundle having a length of 30 cm with warm water at 35 to 40° C., 1 g of the hair cleansing agent of Example 6 was discharged from the aerosol container in the form of foam and coated on the hair bundle, which was cleansed for 60 seconds and then rinsed out with warm water at 35 to 40° C. for 60 seconds. The hair bundle was subjected to this cleansing operation 15 times and then blow-dried, and then p-toluenesulfonic acid remaining in the hair was analyzed, by TOF-SIMS (produced by ION-TOF GmbH).

The cleansing operation was similarly performed by using the hair cleansing agent stock solution of Comparative Example 12 instead of the hair cleansing agent of Example 6, and then p-toluenesulfonic acid remaining in the hair was analyzed.

Figure 2:
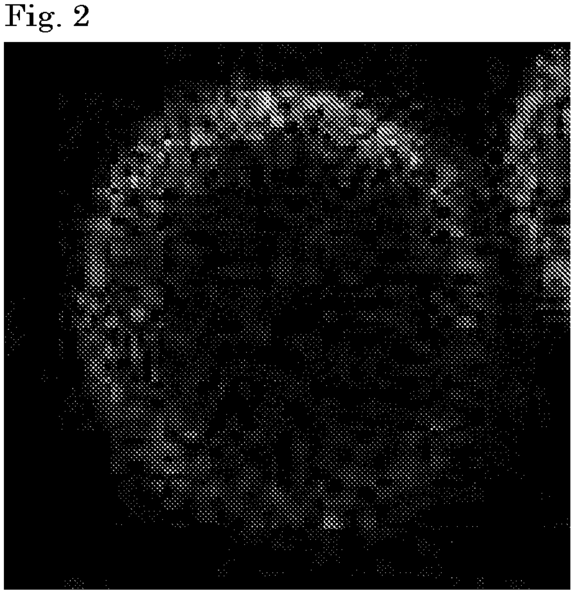
FIG. 2 is a mapping image obtained through analysis by TOF-SIMS of p-toluenesulfonic acid existing on the cross section of the hair cleansed with the hair cleansing agent of Comparative Example 12.

FIGS. 1 and 2 show the penetration state of p-toluenesulfonic acid into the inside of the hair, i.e., the mapping images obtained through analysis by TOF-SIMS of p-toluenesulfonic acid existing on the cross section of the hair cleansed with the hair cleansing agents of Example 6 and Comparative Example 12, respectively. In FIGS. 1 and 2, the bright part shows the existence of p-toluenesulfonic acid.

As shown by the comparison of FIG. 1 and FIG. 2, it is understood that the use of the aerosol type hair cleansing agent of the present invention provides a high penetration effect of p-toluenesulfonic acid into the inside of the hair.

INDUSTRIAL APPLICABILITY

According to the present invention, an aerosol type cosmetic hair preparation that can allow an organic acid, which is an active ingredient for the hair reformation, to penetrate efficiently into the inside of the hair can be provided.

The invention claimed is:

1. An aerosol cosmetic hair preparation comprising a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less, wherein the component (B) comprises p-toluenesulfonic acid or a salt thereof;

said (A) comprises sodium laureth sulfate, ammonium laureth sulfate, and sodium cocoyl glutamate;

said (A) is present in an amount of 0.20 to 15% by mass;

said (B) further comprises succinic acid;

said (B) is present in an amount of 0.3 to 5.0% by mass;

said cosmetic hair preparation stock solution further comprises (D) a polymer;

said (D) comprises a nonionic polymer having a weight average molecular weight (Mw) of 1,000,000 to 3,500,000;

said (D) is present in an amount of 0.02 to 0.5% by mass;

the ratio of succinic acid to p-toluenesulfonic acid in the cosmetic hair preparation stock solution is in a range of 1/0.5 to 1/5, and wherein said aerosol cosmetic hair preparation further comprises 70 to 99% water.

2. The aerosol cosmetic hair preparation according to claim 1, wherein a mass ratio of the component (B) with respect to the component (A) in the cosmetic hair preparation stock solution is 0.005 or more and 20 or less.

3. The aerosol cosmetic hair preparation according to claim 1, wherein the aerosol cosmetic hair preparation is an aerosol hair cleansing agent.

4. The aerosol cosmetic hair preparation according to claim 1, wherein a pH of the aerosol cosmetic hair preparation at 20° C. is 3.0 or more and 4.2 or less.

5. A reformation method of hair, comprising applying the aerosol cosmetic hair preparation according to claim 1 to the hair.

6. An aerosol cosmetic hair preparation comprising a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less, wherein the component (B) comprises p-toluenesulfonic acid or a salt thereof;

said (A) comprises PEG-60 hydrogenated castor oil;

said (A) is present in an amount of 0.20 to 15% by mass;

said (B) further comprises succinic acid;

said (B) is present in an amount of 0.3 to 5.0% by mass;

said cosmetic hair preparation stock solution further comprises (D) a polymer;

said (D) comprises a nonionic polymer having a weight average molecular weight (Mw) of 1,000,000 to 3,500,000;

said (D) is present in an amount of 0.02 to 0.5% by mass;

the ratio of succinic acid to p-toluenesulfonic acid in the cosmetic hair preparation stock solution is in a range of 1/0.5 to 1/5, and wherein said aerosol cosmetic hair preparation further comprises 70 to 99% water.

7. The aerosol cosmetic hair preparation according to claim 6, wherein a mass ratio of the component (B) with respect to the component (A) in the cosmetic hair preparation stock solution is 0.005 or more and 20 or less.

8. The aerosol cosmetic hair preparation according to claim 6, wherein the aerosol cosmetic hair preparation is an aerosol hair cleansing agent.

9. The aerosol cosmetic hair preparation according to claim 6, wherein a pH of the aerosol cosmetic hair preparation at 20° C. is 3.0 or more and 4.2 or less.

10. A reformation method of hair, comprising applying the aerosol cosmetic hair preparation according to claim 6 to the hair.

11. An aerosol cosmetic hair preparation comprising a cosmetic hair preparation stock solution containing a surfactant (A) and an organic acid except for citric acid, or a salt thereof (B), and a propellant (C) containing carbon dioxide, having a pH at 20° C. of 3.0 or more and 5.0 or less, wherein the component (B) comprises p-toluenesulfonic acid or a salt thereof;

said (A) comprises one or more members selected from the group consisting of an anionic surfactant and a nonionic surfactant, wherein said anionic surfactant is one or more members selected from the group consisting of sodium laureth sulfate, ammonium laureth sulfate, and sodium cocoyl glutamate, and said nonionic surfactant is polyoxyalkylene hydrogenated castor oil;

said (A) is present in an amount of 0.20 to 15% by mass;

said (B) further comprises succinic acid;

said (B) is present in an amount of 0.3 to 5.0% by mass;

said cosmetic hair preparation stock solution further comprises (D) a polymer;

said (D) is hydroxyethyl cellulose having a weight average molecular weight (Mw) of 1,500,000 to 2,000,000;

said (D) is present in an amount of 0.02 to 0.5% by mass;

the ratio of succinic acid to p-toluenesulfonic acid in the cosmetic hair preparation stock solution is in a range of 1/0.5 to 1/5, and wherein said aerosol cosmetic hair preparation further comprises 70 to 99% water.

12. The aerosol cosmetic hair preparation according to claim 11, wherein a mass ratio of the component (B) with respect to the component (A) in the cosmetic hair preparation stock solution is 0.005 or more and 20 or less.

13. The aerosol cosmetic hair preparation according to claim 11, wherein the aerosol cosmetic hair preparation is an aerosol hair cleansing agent.

14. The aerosol cosmetic hair preparation according to claim 11, wherein a pH of the aerosol cosmetic hair preparation at 20° C. is 3.0 or more and 4.2 or less.

15. A reformation method of hair, comprising applying the aerosol cosmetic hair preparation according to claim 11 to the hair.

* * * * *